(12) United States Patent
Jonsson et al.

(10) Patent No.: US 11,382,836 B2
(45) Date of Patent: Jul. 12, 2022

(54) MEDICAMENT DISPENSING SYSTEM AND DISPENSING METHOD

(71) Applicant: ASTRAZENECA AB, Sodertalje (SE)

(72) Inventors: Fredrik Jonsson, Stockholm (SE); Lubomir Gradinarsky, Molndal (SE)

(73) Assignee: ASTRAZENECA AB, Sodertalje (SE)

( * ) Notice: Subject to any disclaimer, the term of this patent is extended or adjusted under 35 U.S.C. 154(b) by 0 days.

(21) Appl. No.: 16/630,032

(22) PCT Filed: Jul. 5, 2018

(86) PCT No.: PCT/EP2018/068304
§ 371 (c)(1),
(2) Date: Jan. 10, 2020

(87) PCT Pub. No.: WO2019/011787
PCT Pub. Date: Jan. 17, 2019

(65) Prior Publication Data
US 2020/0383872 A1 Dec. 10, 2020

(30) Foreign Application Priority Data
Jul. 13, 2017 (GB) ..................... 1711262

(51) Int. Cl.
*A61J 7/04* (2006.01)
*A61J 1/03* (2006.01)
(Continued)

(52) U.S. Cl.
CPC ............. *A61J 7/0418* (2015.05); *A61J 1/035* (2013.01); *B65D 83/0463* (2013.01);
(Continued)

(58) Field of Classification Search
CPC ...... A61J 7/0418; A61J 1/035; A61J 2200/30; G16H 40/67; G16H 20/13; B65D 83/0463;
(Continued)

(56) References Cited

U.S. PATENT DOCUMENTS 4,660,991 A 4/1987 Simon
8,448,530 B2 * 5/2013 Leuenberger ......... A61J 7/0418
73/862.625
(Continued)

FOREIGN PATENT DOCUMENTS

EP 2239651 A2 10/2010
JP 61-185267 8/1986
(Continued)

*Primary Examiner* — Michael Collins
(74) *Attorney, Agent, or Firm* — Medler Ferro Woodhouse & Mills PLLC

(57) ABSTRACT

A dispensing system (2) and method for dispensing unit dosage forms (38) from a blister pack (30) is disclosed. The system (2) comprises a housing (4) for receiving a blister pack (30), the blister pack (30) having a plurality of cavities (32) with at least one unit dosage form (38) sealed in each of the cavities (32), the housing (4) comprising at least one housing aperture. The system (2) also comprises a sensing layer comprising a plurality of apertures, each sensing layer aperture configured to substantially align with a corresponding one or more of the plurality of cavities (32) of the blister pack (30) when a blister pack (30) is received in the housing (4) and at least one sensing region. The system (2) further comprises an electronics unit and a power source for providing voltage to the sensing layer. In use, the unit dosage forms (38) are dispensed from the blister pack (30) through the sensing layer apertures and through the at least one housing aperture, for example by application of pressure (P) upon each cavity (32), and the sensing layer senses each unit dosage form (38) being dispensed from the blister pack (30).

23 Claims, 11 Drawing Sheets

(51) Int. Cl.
   *B65D 83/04* (2006.01)
   *G01L 1/14* (2006.01)
   *G01D 5/34* (2006.01)
   *G16H 20/13* (2018.01)
   *G16H 40/67* (2018.01)
   *H04B 1/02* (2006.01)
   *H04B 10/50* (2013.01)

(52) U.S. Cl.
   CPC .............. *G01D 5/342* (2013.01); *G01L 1/142* (2013.01); *G16H 20/13* (2018.01); *G16H 40/67* (2018.01); *A61J 2200/30* (2013.01); *H04B 1/02* (2013.01); *H04B 10/50* (2013.01)

(58) Field of Classification Search
   CPC .......... G01D 5/342; G01L 1/142; H04B 1/02; H04B 10/50
   See application file for complete search history.

(56) References Cited

U.S. PATENT DOCUMENTS

| | | | |
|---|---|---|---|
| 10,375,847 B2* | 8/2019 | Mehregany | A61J 1/035 |
| 11,193,903 B2* | 12/2021 | Mehregany | A61J 1/035 |
| 2005/0256830 A1* | 11/2005 | Siegel | G16H 20/13 |
| 2008/0001737 A1* | 1/2008 | Metry | B32B 7/12 |
| | | | 340/540 |
| 2013/0236635 A1* | 9/2013 | Leuenberger | G06F 3/045 |
| | | | 427/79 |
| 2013/0285681 A1* | 10/2013 | Wilson | A61J 1/035 |
| | | | 324/693 |
| 2016/0000657 A1* | 1/2016 | Dickie | A61J 7/0084 |
| | | | 206/534 |
| 2016/0103085 A1* | 4/2016 | Mehregany | A61J 1/035 |
| | | | 361/679.01 |
| 2016/0132661 A1* | 5/2016 | Dixit | A61J 1/16 |
| | | | 206/531 |
| 2016/0158109 A1 | 6/2016 | Nova | |
| 2017/0172851 A1* | 6/2017 | Schmid | A61J 7/02 |
| 2017/0194961 A1 | 7/2017 | Chang et al. | |
| 2017/0294105 A1* | 10/2017 | Mehregany | G08B 21/24 |
| 2019/0201286 A1* | 7/2019 | Learmonth | A61J 7/0418 |

FOREIGN PATENT DOCUMENTS

| | | |
|---|---|---|
| JP | 4-503344 | 6/1992 |
| WO | 198909042 A1 | 10/1989 |
| WO | 90/05684 | 5/1990 |
| WO | 2012/111034 | 8/2012 |
| WO | 2012111034 A1 | 8/2012 |

* cited by examiner

MEDICAMENT DISPENSING SYSTEM AND DISPENSING METHOD

TECHNICAL FIELD

The present invention relates to a dispensing device or system for dispensing medicament, and in particular to a dispensing device or system for monitoring when a dose of medicament has been dispensed. The present invention also relates to a method of dispensing a medicament, and in particular to a method of monitoring when a dose of medicament has been dispensed.

BACKGROUND OF THE INVENTION

There are many ways to provide a dose of medicament to a patient or other intended recipient of the medicament, particularly when it is desired to provide multiple concurrent and/or subsequent doses of the medicament, for example as part of a treatment regimen or otherwise. A popular and convenient form of medicament is a unit dose, such as a tablet, pill, capsule, etc., for oral consumption by the recipient. Commonly, multiple unit doses are provided to the recipient in a convenient form for dispensing one or more unit doses at a time, for example in a container with a removable closure, or in a sheet having sealed doses in individual compartments, each with a rupturable or frangible cover, often referred to as a blister pack.

Such devices enable the recipient to access their medication in a portable and convenient manner, when they determine a dose is required. However, particularly where medication should be taken frequently, at regular or irregular intervals, the recipient may not remember at the appropriate time that a dose is due to be taken. Even if the recipient does extract and take a dose from the device (at the appropriate time or later when they remember to do so), they may subsequently forget that they have taken a particular dose, and may then take a further dose too soon.

Such non-compliance issues with treatment regimens are a significant problem in healthcare, leading to ineffective treatment and possible complications for the patient who may under or over dose on a medication, potentially limiting the effectiveness of their long term treatment and/or leading to exacerbations, side effects, etc. Furthermore, unused medication from missed doses must be discarded appropriately and according to local restrictions and regulations, which may be costly to implement and inconvenient.

Attempts to overcome the above issues of non-adherence to dosing regimens have been made, for example by marking individual blisters on a blister pack with an indication of when the dose should be taken. However this requires each blister pack to be customised to the recipient's specific needs and dosing regimen. More recent devices and systems have been developed, which generally contain multiple unit doses in compartments from which they can be dispensed and some form of monitoring of the compartments to determine if the unit dose has been removed and (it is implied) that it has been taken by the patient. However, despite several attempts to produce a suitable device or system, the prior art solutions have generally been very expensive to manufacture and consist of several relatively complex components, many of which are used only a single time (i.e. for one dosing period until the unit doses have all been removed) and then must be discarded. If the components of the device comprise electronics as is typically the case, again there are local regulations that must be followed for disposing of such components and the cost of such devices is prohibitively high.

Therefore there remains a need for a medicament dispenser, and a method of dispensing a medicament, that enables a patient or other intended recipient of a medicament, to reliably dispense the medicament at the appropriate time and to be able to review whether, and at what time, they took a particular dose at a time after the event. Furthermore, there remains a need for such a dispenser and method of dispensing that can be provided at an acceptable associated price, and a cost attractive, reliable, reusable, patient and manufacturing friendly adherence monitoring solution has the potential to address one or more of the above mentioned patient needs.

SUMMARY OF THE INVENTION

In accordance with the present invention, there is provided a dispensing system and method, which overcome at least one or more of the drawbacks of the prior art. From a first broad aspect, there is provided a dispensing system for dispensing unit dosage forms from a blister pack, the dispensing system comprising: a housing for receiving a blister pack, the blister pack having a plurality of cavities with at least one unit dosage form sealed in each of the cavities, the housing comprising at least one housing aperture; a sensing layer comprising: a plurality of apertures, each sensing layer aperture configured to substantially align with a corresponding one or more of the plurality of cavities of the blister pack when a blister pack is received in the housing; and a plurality of pressure sensing regions, at least one pressure sensing region at least partially surrounding each sensing layer aperture; an electronics unit; and a power source for providing voltage to the sensing layer; wherein: in use, the unit dosage forms are dispensed from the blister pack through the sensing layer apertures and through the at least one housing aperture by application of pressure upon each cavity; and the sensing layer senses the pressure applied in the vicinity of each cavity as each unit dosage form is dispensed from the blister pack.

The dispensing system is advantageous as a blister pack having doses of a medicament, or the like, sealed in its cavities can be received in the housing of the system and a patient or other recipient of the dose of medicament (or caregiver, etc.) is able to push on a cavity to break the seal of the blister and dispense the dose in the usual manner, and the dispensing system senses the pressure of the patient expelling a dose from a cavity, enabling a reliable and more accurate determination of a dose being dispensed than in the prior art. Furthermore, the modular arrangement of the dispensing system, i.e. the housing being configured for receiving a blister pack, enables the system to be reused many times with replacement blister packs that are replenished as each previous blister pack is emptied. Therefore the electronics unit, for example, is able to be used multiple times, avoiding the cost and environmental issues associated with disposing of electronics after a single or brief use. Similarly the sensing layer can be reused multiple times. Furthermore, as the sensing layer comprises apertures, this enables the blister pack to be inserted on top of the sensing layer in the housing, thus it is easy and convenient for a patient to drop their blister pack into the assembled system.

The system is particularly beneficial for unit dosage forms (pills, tablets, capsules, etc.) that are provided to the patient in standard blister packs, as is the case for many of the medicaments dispensed in many countries. Standard blister packs typically have multiple cavities spaced apart in a regular or irregular array, with a single dose of medicament in each cavity, that can be expelled from the blister pack by collapsing the cavity with pressure (from the patient's finger or thumb, for example) and pushing the dose through a rupturable seal over the cavity. The term "standard" here is intended to indicate prior art blister packs of various sizes, shapes and configurations, that may be specific to a particular medication but are generally mass-produced in a similar form for each medication. Therefore, a user of the system can simply insert a standard blister pack into the housing and dispense the doses at the required times, the system determining the dispensing events so that adherence or non-adherence to a dosing regimen is recorded for further reference. When all doses in a blister have been dispensed, the user simply removes the empty blister pack from the housing and inserts a replacement standard blister pack to continue recording their adherence or otherwise to the treatment regimen. Advantageously, the system may comprise at least one sensor for detecting removal of the empty blister pack and/or insertion of a replacement blister pack and detection thereof enables the system to adjust or update in response to this event, e.g. to reset any counters, displays, etc., and/or to display such information to the user, etc.

As discussed above, the dispensing system uses the pressure applied by the patient to expel a dose to determine when a medicament dose is being taken by the patient. This is achieved using a sensing layer having apertures through which the doses are dispensed and pressure sensing regions. The sensing layer may comprise a pressure sensitive layer that defines the pressure sensing regions and a conductive layer, the conductive layer comprising conductive regions substantially aligned with the pressure sensing regions of the sensing layer. This arrangement is advantageous because voltage can be applied to the conductive layer and when the conductive regions of the layer contact the pressure sensing regions, current flows in the pressure sensing regions enabling the pressure sensing to occur.

The sensing layer may further comprises a spacing layer between the pressure sensitive layer and the conductive layer, the spacing layer spacing the pressure sensitive layer and conductive layer apart such that they are not in electrical contact, and the spacing layer being compressible such that the pressure sensitive layer and conductive layer can be brought into electrical contact. Therefore, when the pressure sensitive layer and conductive layer are spaced apart, any voltage provided to the conductive layer will not be provided to the pressure sensitive layer. However, as the patient pushes on the blister pack cavity to expel a dose, the spacing layer compresses and the pressure sensitive layer and conductive layer are brought into electrical contact so that voltage is provided to the pressure sensing layer and the pressure applied to the blister is determined. This open circuit/switch-type arrangement is particularly advantageous for enabling the use of small power sources in the system and for improving the operational lifetime of the system as the circuit/switch will close only when pressure is applied to the sensing layer and the spacing layer is sufficiently compressed. The spacing layer may comprise foam, which is a material that is readily configurable for the desired compressibility under an appropriate amount of pressure.

The layers of the system may be configured in any suitable manner to achieve the above functions. For example, the sensing layer apertures may be substantially circular or elliptical, and the sensing layer aperture of the spacing layer may have a larger diameter than the sensing layer aperture of the pressure sensitive layer and of the sensing layer aperture of the conductive layer, such that an air gap is provided between the pressure sensitive layer and conductive layer in the vicinity of the apertures. Namely, there is a portion surrounding the apertures of each of the pressure sensitive layer and the conductive layer that is exposed even when in contact with the spacing layer, such that as the spacing layer is compressed, the exposed portions directly contact. The apertures of the pressure sensitive layer may be substantially the same size as the apertures of the conductive layer, or one of these layers may have apertures with larger diameters than those of the other of these layers.

As discussed above, it is desirable to space apart the conductive layer to which voltage may be provided by the power source, from the pressure sensitive layer unless sufficient pressure is applied in use to bring the layers into electrical contact. Thus the sensing layer may be configured such that compression of the compressible spacing layer depletes the air gap until the pressure sensitive layer and the conductive layer are brought into electrical contact. The power source may be a battery, such as a button cell or other small battery device, and or may be rechargeable, which may be via and external source (for example by inductive coupling) and/or may be a solar cell, etc.

The pressure sensitive layer may be configured in any suitable manner such that pressure thereon is registered and/or measured in a suitable form. In particular arrangements, the pressure sensitive layer may comprise a non-conductive material comprising conductive particles dispersed therein. Such materials are typical semi-conductive, allowing current to flow through the material but not to the same extent as a conductive material and are pressure sensitive in that the resistance of the material changes (typically decreases) as pressure is applied to the material, since the dispersed conductive particles are compressed more closely together. Therefore changes in the resistance of the material can be measured at one or more different positions in the material to determine where and how much pressure is being applied to the material. Particularly useful materials for the pressure sensitive layer are those that are flexible and relatively low cost, such as materials that comprise a polymer film layer, preferably a polyolefin, such as polyethylene, layer, impregnated with conductive particles, preferably carbon black particles. Examples of suitable materials include Velostat® and Linguist® and Eeonyx®. Velostat® for example, is particularly useful being thin, flexible, and easy to manufacture into the desired layers (which can be cut to shape and apertures cut therethrough). However any suitable material with appropriate properties may be used.

The conductive layer may be configured in any suitable manner such that voltage can be provided to/from the layer. Particularly for low cost dispensing systems, it is desirable for the conductive layer to be simple to manufacture and mass produce. Therefore the conductive layer may comprise a printed circuit board (PCB). Such printed electronics are convenient, easy to configure, low cost and readily printed on thin and/or flexible materials which are very suitable for use in the present system. In certain arrangements for example, where it is desired to determine a particular location where pressure is applied, the conductive regions of the conductive layer may be substantially ring-shaped and encircle the apertures in the conductive layer, each conductive region being discrete from any other conductive region of the conductive layer. Thus pressure at or around a particular blister can be discerned as the resistance change (for example) of the material at a particular location can be detected. Such conductive regions could be printed around each aperture, with traces connecting each aperture to control electronics or the like. Alternatively, for ease of manufacture, the conductive regions of the conductive layer may comprise substantially all of the conductive layer. Thus a substrate for example could have an entire coating of conductive material applied (or indeed the layer may substantially comprise conductive material) and the appropriate apertures could be cut from the layer to form the conductive layer.

The housing of the dispensing system comprises at least one housing aperture. This allows pills or the like to be pushed from a blister cavity and through the aperture in the housing. The housing aperture may, for example, cover substantially all of the base of the housing, with just a frame around the outside of the aperture defining the housing base. This enables blister packs of different configurations to be used with the housing since the housing aperture is large and aligns with all the blisters. However to provide more structural rigidity to the housing, the housing may comprise a base comprising a plurality of housing apertures, the housing apertures arranged in an array such that each housing aperture substantially aligns with at least one of the plurality of cavities of a blister pack when a blister pack is received in the housing, the blister pack being a standard blister pack. The housing apertures may be configured so as to be substantially the same size (or slightly larger) than the footprint of each blister and in a corresponding pattern, so as to match the particular blister pack. Alternatively, the housing apertures may be substantially larger than the footprint of each blister and configured to correspond with several blisters of a blister pack. In some arrangements, the base portion of the housing may be removable and replaceable with a base portion having apertures of a different configuration, to enable the housing to be customised to different blister packs.

The dispensing system comprises an electronics unit and a power source. The electronics unit may comprise components such as a processor, for processing received signals indicative of pressure being applied to the sensing layer, etc. Therefore the electrical system of the dispensing system is an active system, compared with a passive system of some prior art arrangements. The electronics unit may comprise a memory for storing data corresponding to at least the time and date at which the sensing layer senses the pressure applied in the vicinity of each cavity as each unit dosage form is dispensed from the blister pack. The electronics unit may further comprise a transmitter, which may be a wireless transmitter, which may be a Bluetooth LE transmitter, for transmitting data to a remote device, the data corresponding to at least the time and date at which the sensing layer senses the pressure applied in the vicinity of each cavity as each unit dosage form is dispensed from the blister pack and/or the data corresponding to a reminder that a unit dosage form is due to be dispensed at a predetermined date and time. Other transmitters are contemplated in other embodiments of the present invention, for example those that communicate via other wireless protocols, including WiFi, 3G, 4G, 5G, etc. Thus information relating to when a blister has been pressed and a dose therefore dispensed can be transmitted to an external device such as a computer, smartphone, smartwatch, printer or the like and the patient or caregiver is able to see data relating to whether the patient has followed their dosing regimen, and whether there are particular times where the patient has not, etc.

The dispensing system may comprise other components, for example within the electronics unit, to aid the system in efficient operation. The system may comprise an accelerometer, thus the system can determine when the user is handling the dispensing system for example. The accelerometer may be configured to determine when a level of activity above a certain threshold is detected and therefore that it is likely that the user is about to dispense a dose. The system may use this determination to wake up the necessary components of the device for detecting dispensing of a dose, and/or for selecting an appropriate algorithm for determining if a dose is dispensed, etc. The accelerometer may also be configured to determine when a level of activity below a certain threshold is detected and therefore that it is likely the dispensing system has been put away by the user. The system may use this determination to shut down any components that are not required for the underlying operation of the system, such as those for detecting dispensing of a dose (i.e. the system may switch to a sleep mode to conserve power).

As discussed above, a reminder may be transmitted to a remote device, for example to the patient's smartphone or smartwatch, to remind them when it is time to take a dose of medication so as to help them follow the dosing regimen. Additionally or alternatively, a reminder may be generated at the remote device, based on the information provided from the dispensing system. The reminder could be in the form of a message displayed on the remote device, an alarm, a visual indication such as a light flashing and/or a vibrational alert. It may additionally or alternatively be useful for the patient to receive a reminder at the dispensing system itself. Therefore the dispensing system may comprise a display for displaying a reminder and/or other useful information, and/or may comprise other means for indicating when a dose is to be dispensed such as a light that is illuminated to indicate a dosage time, and/or a vibrational alert, and/or an audible alarm, etc. The dispensing system display may additionally or alternatively display other information, for example the display may display the data discussed above, such as when pills have been taken or missed, etc.

The sensing layer of the dispensing system senses the pressure applied as a dose is dispensed from a blister pack inserted into the dispensing system. Whilst the dispensing system may be configured to determine any pressure in the vicinity of a cavity as a dispensing pressure, it might be that the pressure is not sufficient to dispense a dose of medication and/or the pressure is not due to deliberate application by the patient of pressure to dispense a dose. For example, if a patient carries a dispensing mechanism in a pocket, wallet, purse, bag, etc., then inadvertent pressure may be applied to the dispensing device from contact with other objections in the bag, etc., or as the patient moves around, and so on. Therefore it is desirable to determine if pressure applied to the dispensing system is likely to be to dispense a dose, or for other reasons. The sensing layer may therefore sense the profile of the pressure applied in the vicinity of each cavity, to determine if a unit dosage form has been dispensed from the blister pack; or the pressure has a non-dispensing pressure profile. For example, a threshold may be determined for the sensed pressure, above which it is determined that it is likely a dose was dispensed. Where the pressure sensitive layer comprises a semi-conductive material, for example, a measure of a resistance below a certain threshold may indicate a sufficient amount of pressure to dispense a dose. Additionally or alternatively, the shape of the pressure and/or its location(s) may be used to determine if a dose has been dispensed. For example, if the sensing layer senses pressure in multiple locations (perhaps of generally of the same order of magnitude at each location) then the system may determine this is more likely to be due to the dispensing system being squashed against other items in a bag, or being in a pocket, etc. By analysing a pressure pattern, for example pressure magnitude, distribution of pressure (if one side of the aperture receives higher pressure than other sides), pressure profile (i.e. how fast pressure builds up and releases), etc., the dispensing system can determine if a pill is taken. The algorithm can be implemented inside the electronics unit, or mechanically for example by adjusting the thickness of the foam and the rigidity of sensor structure to only give an indication if sufficient pressure is applied.

As discussed above, a modular dispensing system is advantageous because many of the components of the system are reusable with multiple successive blister packs. Certain of the components of the dispensing system may be more durable than other of the components. For example the housing may be formed from plastic and very rarely require replacing. Other components of the system may require more frequent replacement if, for example, the power source expires. However, in some arrangements, a replaceable and/or rechargeable battery is provided. The sensing layer may be relatively durable and not need regular replacement but it may be desirable, in optional configurations, to customise the configuration of the sensing layer for different blister packs, even if they are standard blister packs since these may have variations in their configuration and differ depending on the particular medication, etc. Therefore the housing and the sensing layer may be separable components and are configured such that sensing layers with different configurations are each receivable in the housing. The patient can then extract the existing sensing layer and drop in a replacement sensing layer to modify the dispensing system as desired. The electronics unit may be substantially enclosed within the housing, the housing having a connection opening to receive a connector of the sensing layer for connection to the electronics unit. This protects the electronics unit from damage and dirt, etc., improving the lifetime of the electronics unit. However the housing may be configured such that the enclosure can be opened to access the electronics unit or other parts of the system, to replace the power source and/or any component of the electronics unit, and/or the entire electronics unit. Therefore the system is configurable, updatable and/or upgradable and more flexible than prior art arrangements and prevents unnecessary discarding of system components.

From a further broad aspect, there is provided a method of dispensing unit dosage forms from a dispensing system having a blister pack received therein, the dispensing system comprising: a housing for receiving a blister pack, the blister pack having a plurality of cavities with at least one unit dosage form sealed in each of the cavities, the housing comprising at least one housing aperture; a sensing layer comprising: a plurality of apertures, each sensing layer aperture configured to substantially align with a corresponding one or more of the plurality of cavities of the blister pack when a blister pack is received in the housing; and a plurality of pressure sensing regions, at least one pressure sensing region at least partially surrounding each sensing layer aperture; an electronics unit; and a power source for providing voltage to the sensing layer; the method comprising: sensing with the sensing layer pressure applied in the vicinity of each cavity as each unit dosage form is dispensed from the blister pack through the sensing layer apertures and through the at least one housing aperture. The dispensing system used in the method may have any one or more of the features discussed above in accordance with the first broad aspect of the present invention. For example, the sensing layer of the dispensing device may further comprise a spacing layer between the pressure sensitive layer and the conductive layer, the spacing layer spacing the pressure sensitive layer and conductive layer apart such that they are not in electrical contact, and the method further comprising bringing the pressure sensitive layer and conductive layer into electrical contact by compressing the spacing layer.

The sensing layer apertures may be substantially circular or elliptical, and the sensing layer aperture of the spacing layer may have a larger diameter than the sensing layer aperture of the pressure sensitive layer and of the sensing layer aperture of the conductive layer, such that an air gap is provided between the pressure sensitive layer and conductive layer in the vicinity of the apertures, the method further comprising compressing the compressible spacing layer to deplete the air gap to bring until the pressure sensitive layer and the conductive layer into electrical contact.

The method may further comprise providing voltage to the conductive layer from the power source. The method may further comprise storing data corresponding to at least the time and date at which the sensing layer senses the pressure applied in the vicinity of each cavity as each unit dosage form is dispensed from the blister pack in a memory of the electronics unit. The method may further comprising detecting and/or storing other useful information, such as an identification (ID) of the blister pack inserted in the housing (which ID may, for example, be detected from a chip or tag of the blister pack that has the ID stored therein), and/or information relating to a blister pack being removed and/or inserted, and/or information related to the orientation of the blister pack, etc. The method may further comprise transmitting data to a remote device, the data corresponding to at least the time and date at which the sensing layer senses the pressure applied in the vicinity of each cavity as each unit dosage form is dispensed from the blister pack and/or the data corresponding to a reminder that a unit dosage form is due to be dispensed at a predetermined date and time. The method may further comprise transmitting data wirelessly, preferably comprising Bluetooth LE transmission.

The method may further comprise displaying the data on a display of the dispensing system. The method may further comprise sensing a profile of the pressure applied in the vicinity of each cavity, to determine if: a unit dosage form has been dispensed from the blister pack; or the pressure has a non-dispensing pressure profile.

BRIEF DESCRIPTION OF THE DRAWINGS

Preferred aspects and embodiments of the present invention will now be described, by way of example only, with reference to the accompanying drawings, in which.

DETAILED DESCRIPTION OF PREFERRED EMBODIMENTS

Dispensing systems (and methods) in accordance with embodiments of the present invention are configured for dispensing unit doses from a blister pack, typically a standard blister pack. Blister packs are considered to be standard blister packs when, for example, a particular medicament is dispensed in blister packs that typically remain of the same configuration for a prolonged period of time, e.g. are mass produced, and/or have a standard arrangement of multiple cavities, etc. A typical standard blister pack comprises flat sheet(s) of foils (covering each other and being attached to each other). One, relatively rigid foil, most commonly called the base, comprises cavities or open "blisters", for accommodating a tablet or capsule each, while the other foil is flat and most commonly called the lid, and seals the opening of the cavities or blisters. The most commonly used sealing process is heat sealing, at least one of the foils having thermoplastic properties, and at present the manufacture of the pack is most rationally carried out by continuously joining webs of the foils for said sealing, and cutting them to said packs. Whereby depressing the blister from the top will cause the medication to puncture through the lid foil so that the medication is freed from the pack to be taken by the patient.

Figure 1:
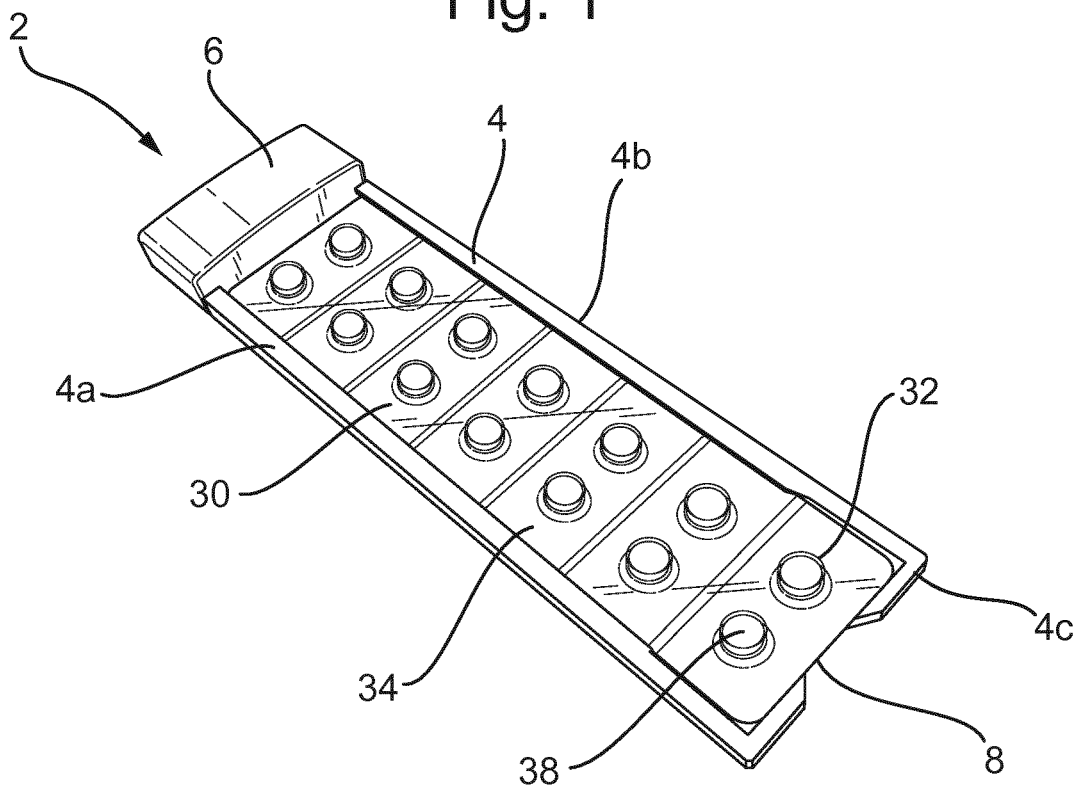
FIG. 1 is a perspective view of a dispensing system with a blister pack received therein, in accordance with embodiments of the present invention.

Referring to FIG. 1, a dispensing system 2 in accordance with embodiments of the present invention is illustrated, the dispensing system 2 having a blister pack 30 received in the housing 4 of the dispensing system 2. The blister pack comprises a blister base 34, having a plurality of cavities 32 formed therein and each cavity 32 contains a unit dose 38 of medicament. The cavities 32 are sealed with a frangible layer 36 (not shown—see FIG. 3). The housing 4 is of a suitable size and shape to receive the blister pack 30 securely between the side edges 4a, 4b of the housing 4 and a cover 6 at one end and an end edge 4c at the other. A cut out 8 is provided in the end edge 4c to aid the patient in lifting out the blister pack 30 when it is desired to replace it with a new blister pack 30.

The cover 6 of the housing 4 encloses an electronics unit 10. In the illustrated arrangement, there is provided an opening in the cover 6 through which a connection to a connector 12 of the electronics unit 10 (not shown—see FIG. 3) can be made. However in other arrangements the electronics unit and the sensing component(s) can be manufactured on the same printed circuit board. Typically the housing is formed from plastic, or other suitable material.

Figure 2:
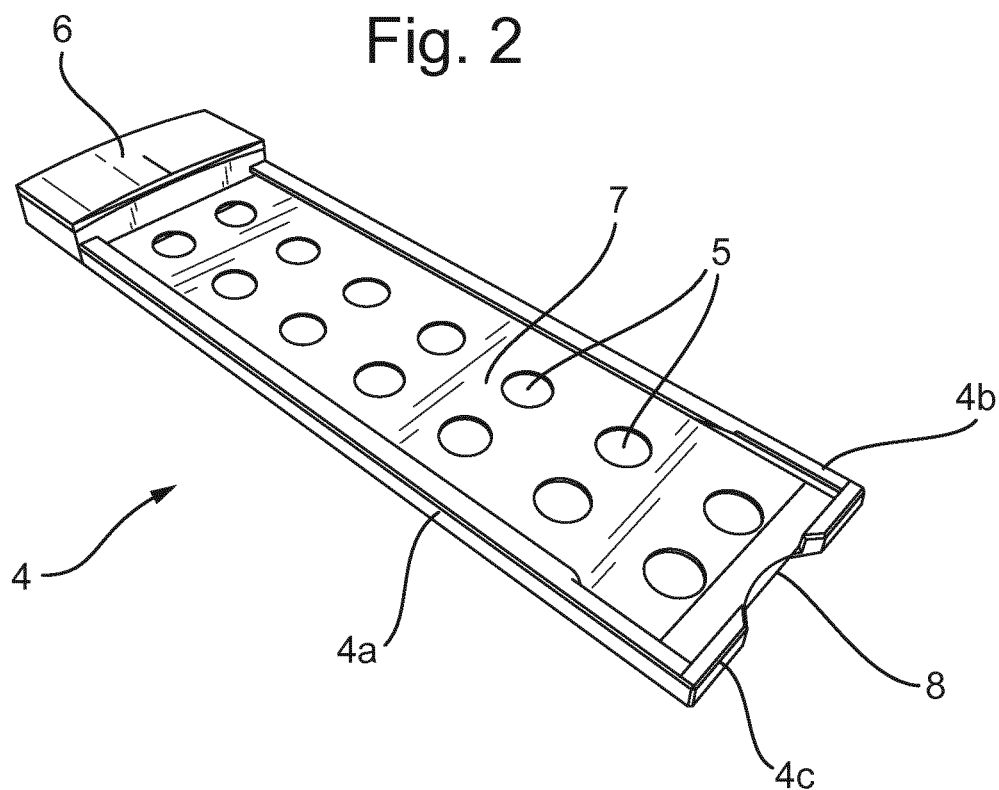
FIG. 2 is a perspective view of the dispensing system of FIG. 1, without a blister pack.

The housing 4 is illustrated in FIG. 2 with the blister pack 30 removed. The housing 4 comprises a plurality of apertures 5, which in the FIG. 2 embodiment are arranged in a regular array of two by seven apertures 5, though of course other arrangements are possible in other embodiments. Thus one aperture 5 corresponds with each cavity or blister 32 of the blister pack 30 of FIG. 1. Therefore a dose 38 from each blister 32 can be pushed out through an aperture 5 in the housing 4 to be dispensed to the patient. The base 7 of the housing 4 may be integrally formed with the housing 4 (e.g. the entire housing may be moulded or the like as a single component) or the base 7 may be removable from the rest of the housing 4, for example it may be slidable away from the cover 6 end or may be liftable away from the housing 4. This enables alternative bases 7 to be inserted into the rest of the housing 4, for example those having a different number and/or arrangement of apertures 5, thereby enabling a different type of blister pack 30 to be used with the same housing 4. Alternatively, the housing 4 may comprise only a single aperture 5, the aperture being of a size so as to substantially define the base 7, thus enabling all doses 38 to be dispensed from each blister 32 through the singe aperture 5. Alternatively the housing 4 may comprise two or more apertures 5, which are sufficiently sized to correspond with more than one blister 32.

Figure 3:
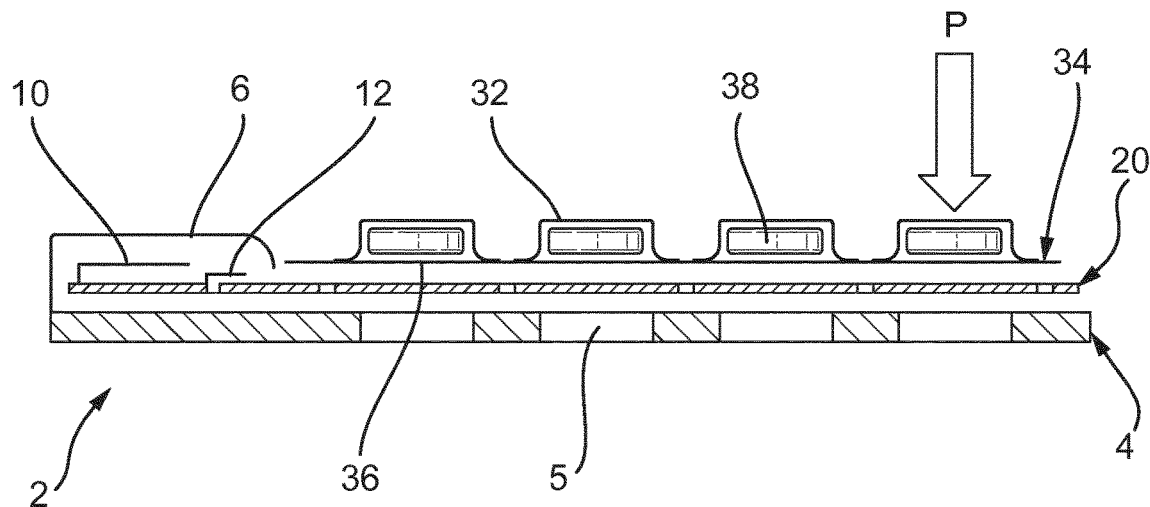
FIG. 3 is a schematic side view of a portion of the dispensing system of FIG. 1.

Referring now to FIG. 3, there is shown a portion of a dispensing system 2 such as that illustrated in FIG. 1, from a side sectional view. Only the four blisters 32 and doses 38 nearest the cover 6 end are shown as is the corresponding portion of the housing 4. The housing apertures 5 can be seen to be aligned with the blisters 32, thus enabling the doses 38 in the blisters 32 to be expelled through the apertures 5. To dispense a dose 38, the patient simply pushes downwards on the blister 32 with a finger or thumb, for example (as indicated by arrow P showing the general direction of pressure from the patients finger or thumb), which in turn pushes the dose 38 into contact with the seal 36. As the seal 36 is configured to be frangible or rupturable, pressure from the dose bursts the seal and the dose 38 drops out, through a corresponding aperture 23, 25, 27 (not shown—see FIG. 4) in the sensing layer 20 and through the corresponding aperture 5 in the housing 4. As also shown in FIG. 3, the electronics unit 10 is enclosed in the housing cover 6, with an opening to enable the sensing layer to be inserted into the cover 6 for connection with a connector 12 of the electronics unit 10. Thus, voltage from a power source can be provided to the sensing layer 20, or at least a portion or layer thereof as discussed further below.

Figure 4:
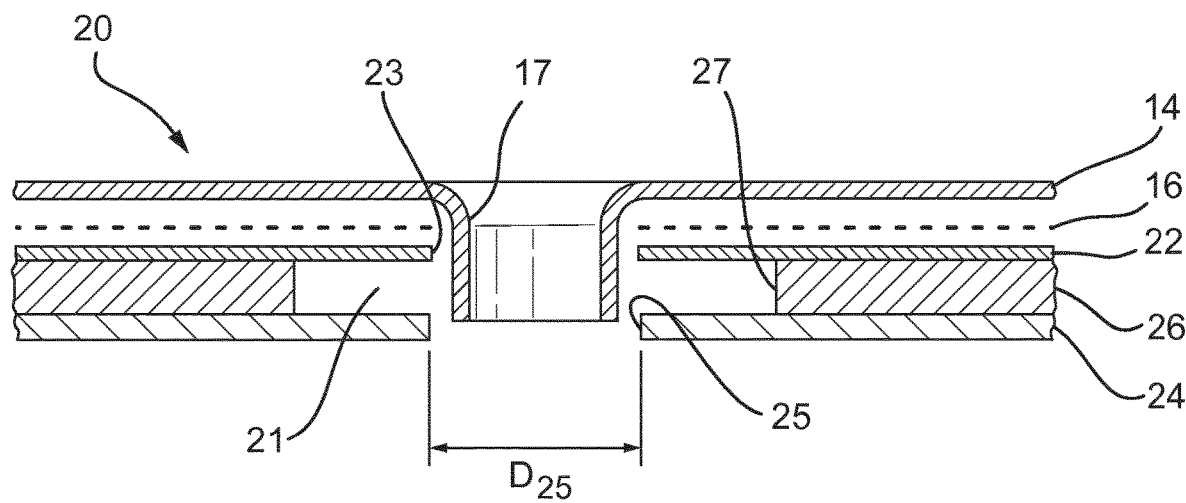
FIG. 4 is a schematic view of a portion of the layers of a sensing layer of a dispensing system in accordance with embodiments of the present invention.
Figure 5A:
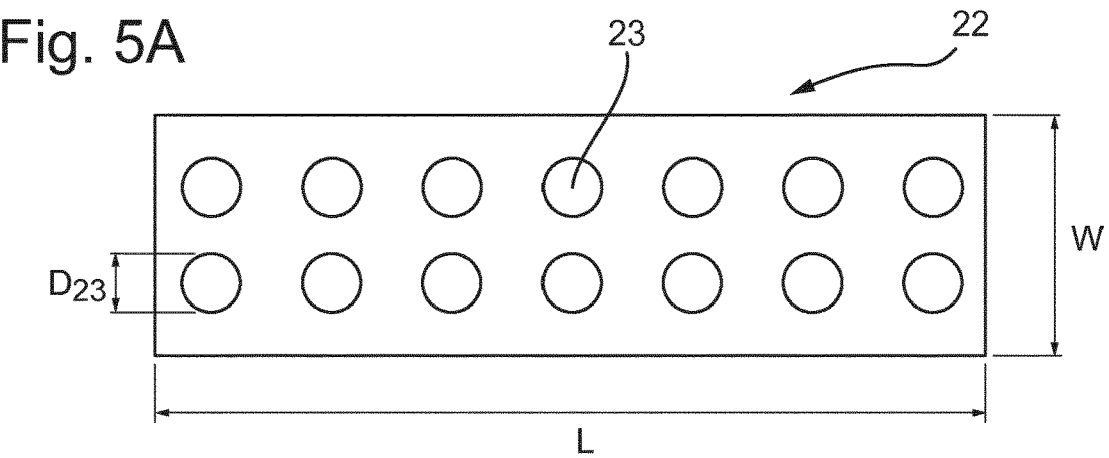
FIGS. 5A to 5D are schematic top views illustrating embodiments of the layers of the sensing layer of FIG. 4.
Figure 5B:
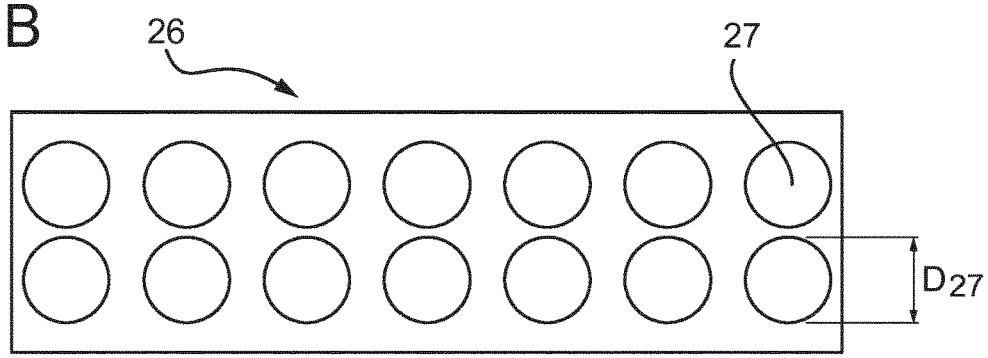
Figure 10:
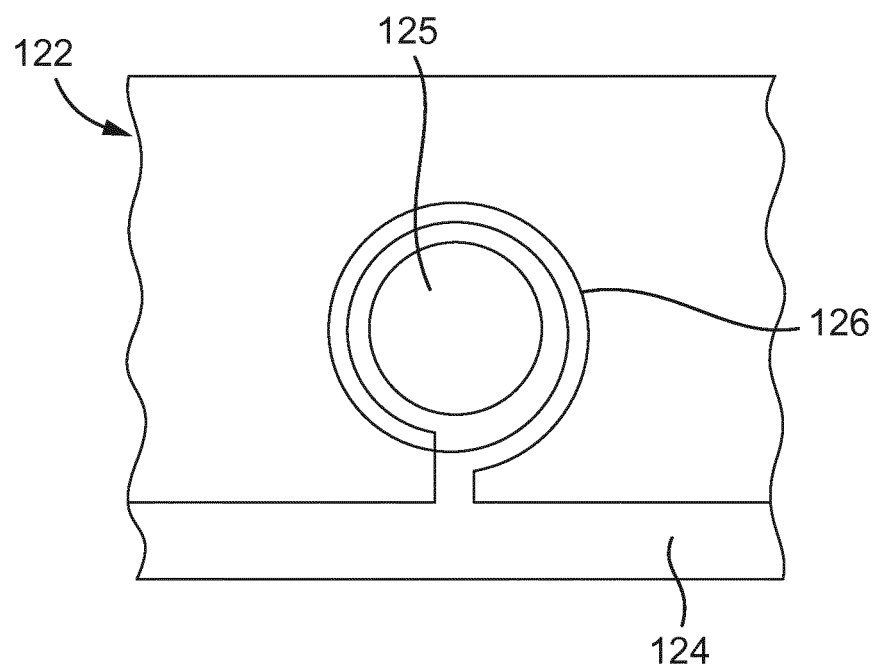
FIG. 10 is a schematic top view of an inductive sensing layer in accordance with alternative embodiments of the present invention.

FIG. 4 illustrates a portion of the sensing layer 20 that, in use with a blister pack 30 inserted in the dispensing system 2 containing the sensing layer 20, would be aligned with a single blister 32 of the blister pack 30. The sensing layer 20 comprises multiple component layers, including a pressure sensitive layer 22, a conductive layer 24 and a compressible foam layer 26 separating the pressure sensitive layer 22 from the conductive layer 24. The pressure sensitive layer 22 is shown in FIG. 5A and is formed from a material that has at least one property that changes as pressure is exerted in the layer 22. For example, the layer 22 may comprises a semi-conductive layer comprising a polymer with conducting particles dispersed therein, which changes resistance as pressure is applied (typically the resistance decreases with applied pressure). Preferred materials for use for the sensing layer 24 include Velostat® and the like. Other sensing methods may be used, which are illustrated in FIGS. 10 to 12 for example, and include capacitive, inductive, piezo electric and optical sensing and are discussed further below. The pressure sensitive layer 22 comprises a plurality of apertures 23 for allowing a dose 38 to pass therethrough. The apertures 23 each have a diameter $D_{23}$ that is larger than the largest dimension of a dose 38 in the blister pack 30. The pressure sensitive layer 22 is dimensioned to fit in the housing 4 and be retained therein, having an appropriate length L and width W.

Figure 5C:
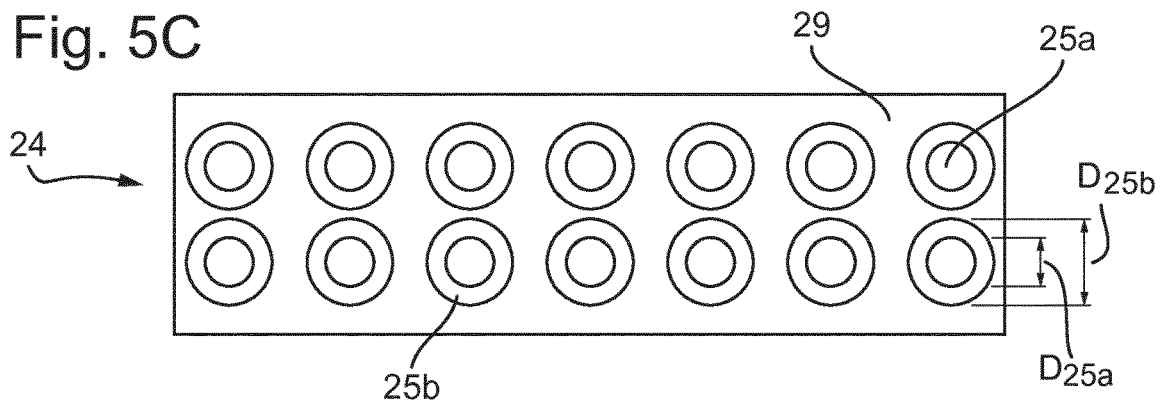
Figure 5D:
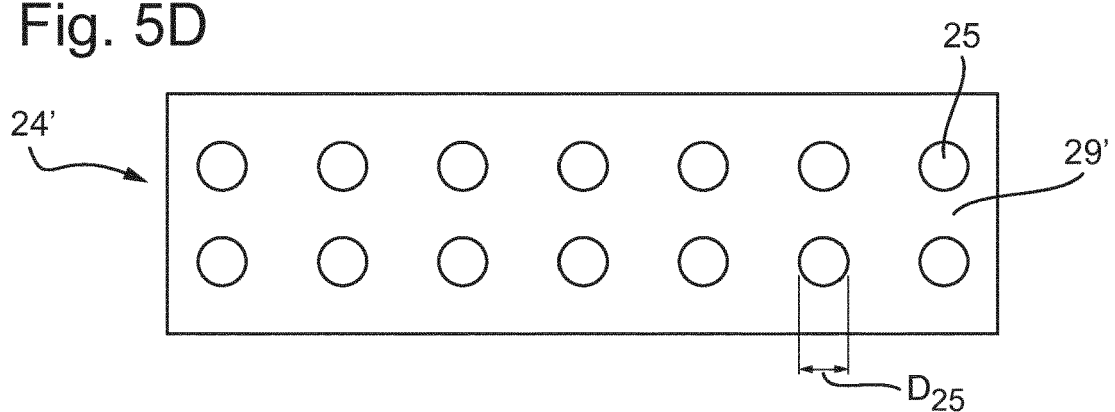
Figure 6:
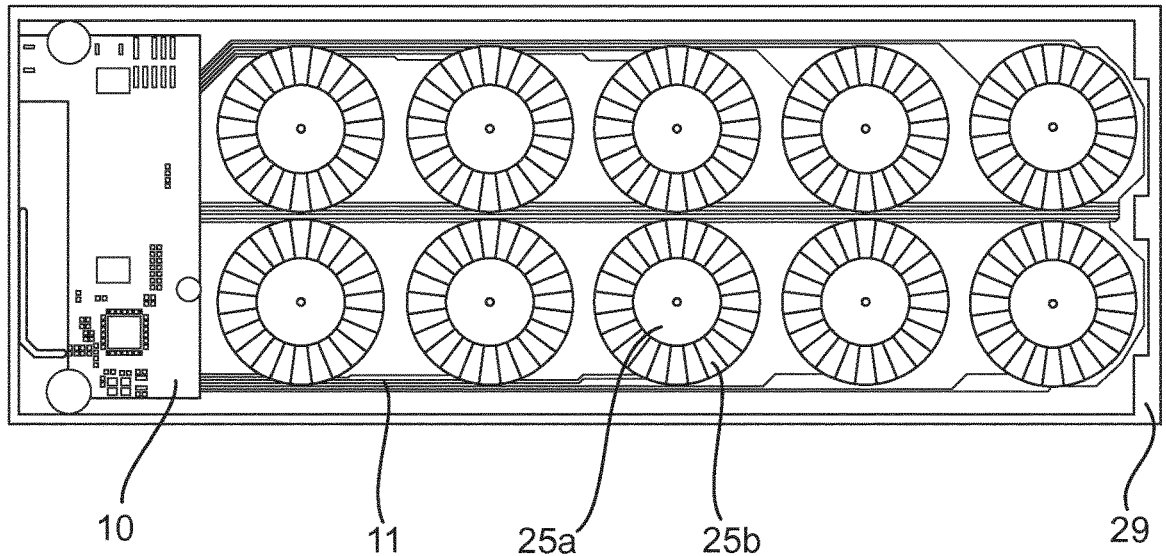
FIG. 6 is a schematic view of a conductive layer of a dispensing system in accordance with embodiments of the present invention.

Two different conductive layers 24, 24' are shown in FIGS. 5C and 5D respectively. Other configurations are also contemplated and discussed below with regard to FIGS. 9A to 9C and FIGS. 13 and 14, for example. The first conductive layer 24 of FIG. 5C comprises a substrate 29, for example of glass-reinforced epoxy laminate, glass fibre, or other suitable substrate material, with conductive regions $25b$ printed or otherwise provided thereon. The conductive regions $25b$ are generally ring-shaped or tablet-shaped (e.g. adapted to be substantially the same shape and slightly larger than the tablet of the particular blister pack) and surround the apertures 25 of the conductive layer 24. The conductive regions $25b$ are formed of any suitable material such as copper, for example. The conductive layer 24 may comprise a printed circuit board (PCB) as shown in FIG. 6, having apertures $25a$ surrounded by conductive regions $25b$ and traces 11 connecting the conductive layers to the electronics unit 10, etc., all printed onto a substrate 29 or etched to expose the conductive regions and traces. This arrangement provides discrete conductive regions $25b$ which can transmit voltage to the pressure sensitive layer 22 when in contact with that layer in the vicinity of the sensing layer apertures 23, 25, 27. The diameter $D_{25b}$ of the conductive regions $25b$ is larger than the diameter $D_{25a}$ of the apertures $25a$.

The alternative conductive layer 24' of FIG. 5D is formed from conductive material, for example from a copper sheet or other suitable material, or may be formed from a substrate with a layer of conductive material printed thereon (not shown). The diameter $D_{25}$ of the apertures 25 is generally the same as those of the FIG. 5C embodiment.

A spacing layer 26 is provided between the pressure sensitive layer 22 and the conductive layer 24, 24'. This spacing layer 26 is compressible, being made of compressible foam for example, and whilst it spaces the pressure sensitive layer 22 apart from the conductive layer 24, 24' when no pressure is applied, pressure from a user dispensing a dose 38 from a blister 32 compresses the spacing layer 26 and brings the pressure sensitive layer 22 and the conductive layer 24, 24' into electrical contact. The apertures 27 of the spacing layer 26 are configured to enable the pressure sensitive layer 22 and the conductive layer 24, 24' to make contact, since the apertures 27 of the spacing layer 26 have a diameter $D_{27}$ larger than the diameters $D_{23}$, $D_{25}$, $D_{25a}$ of the apertures 23, 25, 25a of the pressure sensitive layer 22 and of the conductive layer 24, 24'. Namely an air gap 21 is formed adjacent the edges of the spacing layer 26 surrounding the aperture 27 which exposes the surface of the pressure sensitive layer 22 in the region of the aperture 23 of that layer to the surface of the conductive layer 24, 24' in the region of the aperture 25 of the conductive layer (i.e. exposes the conductive region $25b$ of the embodiment of FIG. 5C). Thus, as the pressure sensitive layer 22 and the conductive layer 24, 24' are compressed towards each other, the exposed regions can be brought into direct electrical contact. Therefore current from the conductive layer 24, 24' can flow through the pressure sensitive layer 22 and into a conductive contact layer 16 and back through the pressure sensitive layer 22 and further back into the conductive layer 22, 24' as the circuit is closed by the layers contacting each other under deformation. This will be discussed in further detail below in relation to FIG. 9.

Figure 9A:
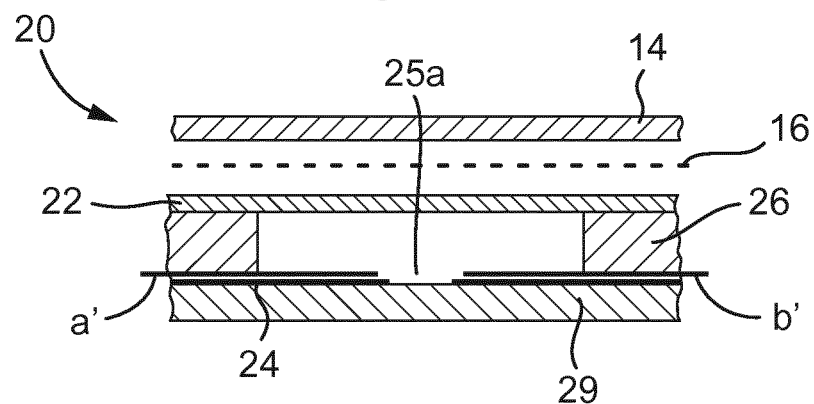
FIG. 9A is a schematic side view of a portion of the layers of a sensing layer of a dispensing system in accordance with alternative embodiments of the present invention.

As shown in FIG. 4, on top of the above three layers 22, 24, 26 additional layers are provided in this embodiment, including a protective plastic layer 14, formed of polyethylene terephthalate (PET) for example, and the additional conductive layer 16, hereinafter referred to as a contact layer 16 for ease of reference. The contact layer 16 is arranged above the pressure sensitive layer 22 and is formed of a conductive material, such as carbon (e.g. graphite) or aluminium, etc., preferably being flexible and thin. A broken portion 17 of the protective layer 14 may extend into the apertures 23, 25, 27 of the three main sensing layer 20 layers in use, or (as shown in FIG. 9) the protective layer 14 may simply flex and not break, providing further protection to the system (if the protective layer 17 is above the dosage being dispensed). The broken portion 17 of the protective layer 14 in the FIG. 4 arrangement covers the contact layer 16 and protects the contact layer 16 and the edges of the apertures 23, 25 of the pressure sensitive layer 22 and the conductive layer 24, 24' (and thus the airgap 21) from dirt and other contaminants. Similarly the unbroken portion of the protective layer 14 of FIGS. 9A and 9C protects the contact layer 16, etc.

Figure 9B:
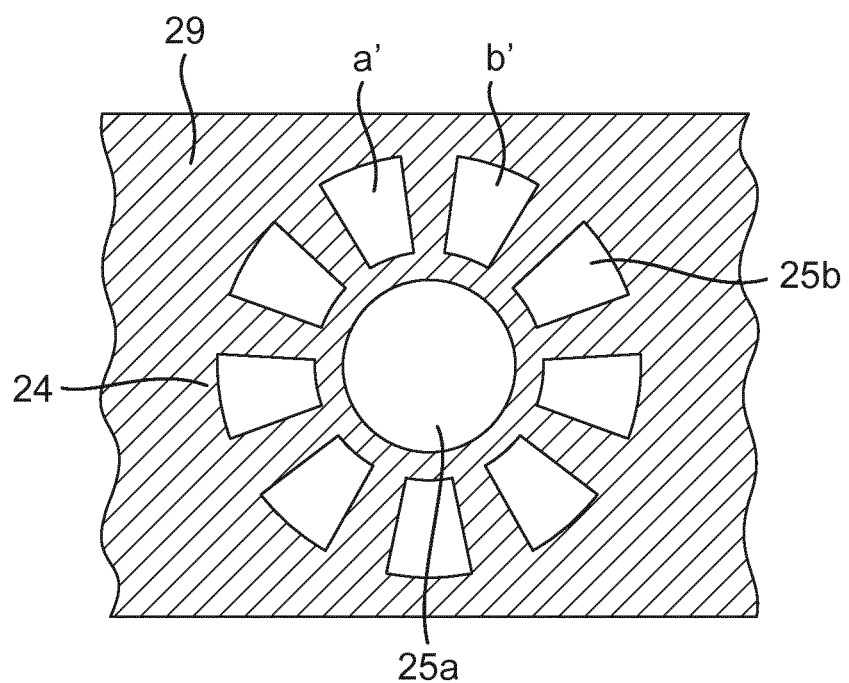
FIG. 9B is a schematic top view of a portion of the conductive layer of FIG. 9A with conductive regions surrounding a conductive aperture.
Figure 9C:
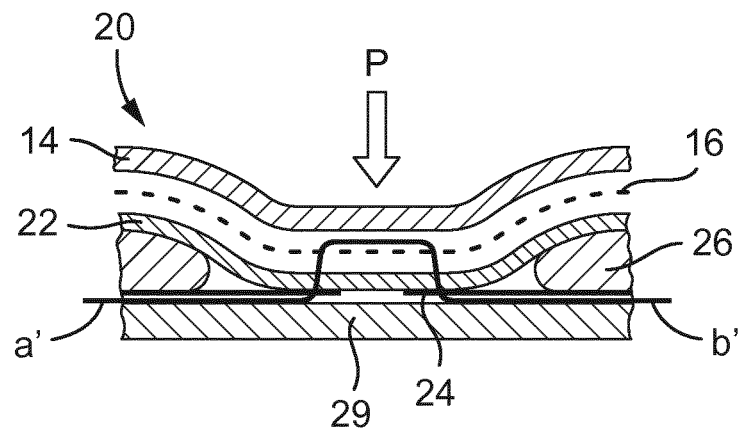
FIG. 9C is a schematic side view of the dispensing system layers of FIG. 9A in a compressed state as a dose is dispensed.

FIGS. 9A to 9C illustrate a portion of a sensing layer in accordance with alternative embodiments of the present invention. This arrangement again includes a conductive layer 24 and the layer 24 is arranged on a substrate 29, the substrate comprising glass fibre. The conductive layer 24 is printed on the substrate 29 as is known in a standard PCB arrangement (which is shown in FIG. 9B). The conductive layer 24 comprises at least one aperture $25a$, with conductive regions $25b$ arranged around the aperture, though in this embodiment, the conductive regions $25b$ are isolated from each other and do not form a solid ring around the aperture $25a$, but are generally arranged in a ring shape. The substrate 29 also includes appropriate apertures (not shown in the Figures). The sensing layer 20 of FIG. 9A further comprises other layers in a similar manner to earlier embodiments, including a foam layer 26, a pressure sensitive layer 22, comprising Velostat or other suitable material, a contact layer 16, of carbon or the like, a protective layer 14, of PET or the like, etc.

As illustrated in FIG. 9C, when it is desired to dispense a unit dose such as a tablet, downward pressure P is applied to a dose inside a blister (not shown) and this pressure P compresses the layers of the sensing layer 20, particularly the foam layer 26. The layers are thus brought together and conductive layer 24 contact the pressure sensitive layer 22, which in turn contacts the contact layer 16. As illustrated by the line a'a-b', voltage applied to the conductive layer 24 can therefore pass through the conductive layer 24 to the pressure sensitive layer 22 and into the contact layer 16, then back through the pressure sensitive layer 22 into the conductive layer 24. Comparing FIG. 9C with FIG. 9A, the circuit is closed in FIG. 9C due to the pressure P and voltage passes through the pressure sensitive layer 22, thereby enabling a determination of pressure being applied and where it is applied (particularly due to the isolated conductive regions 25b shown in FIG. 9B), whereas in FIG. 9A, absent any pressure, the circuit is open and no voltage passes to the pressure sensitive layer 22.

Figure 7:
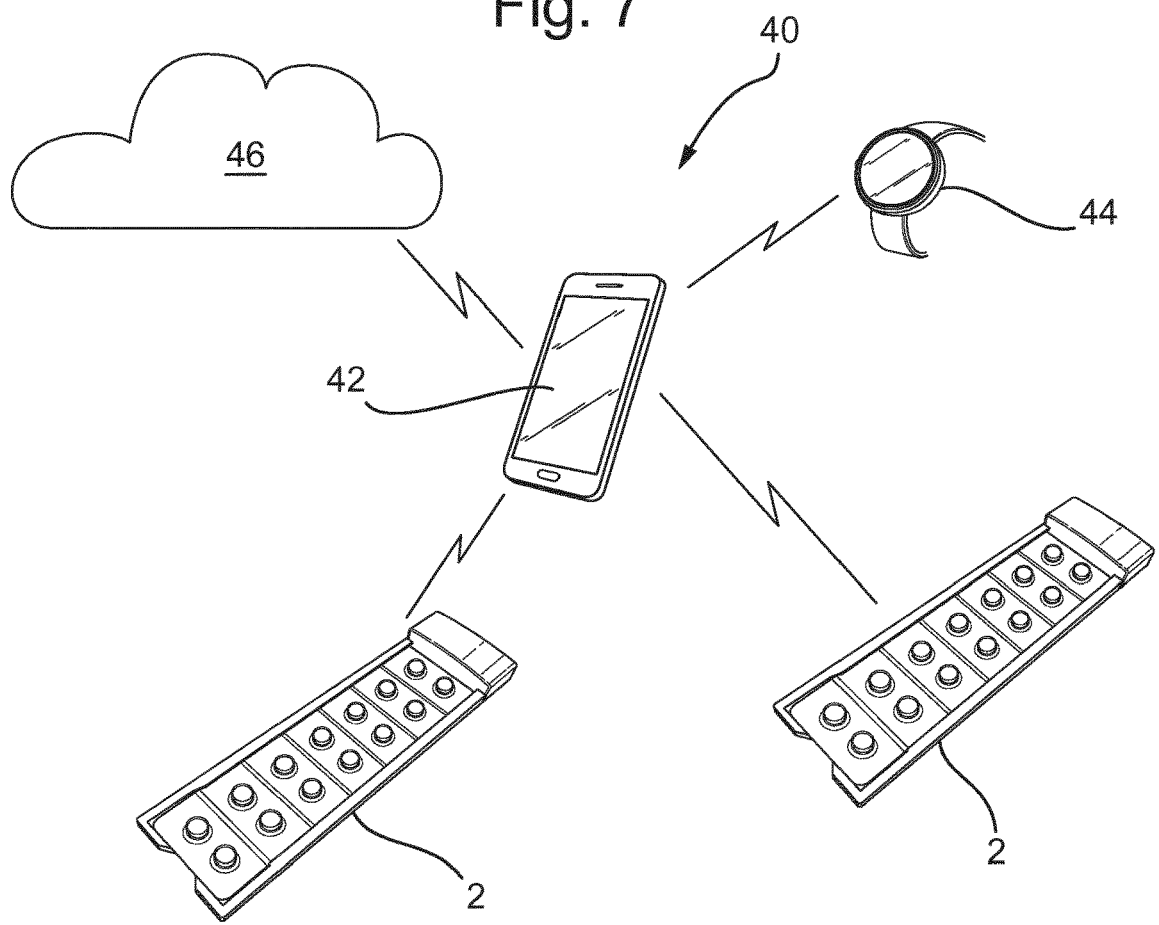
FIG. 7 is a schematic view of a communications network for dispensing systems in accordance with embodiments of the present invention.

Referring now to FIG. 7, dispensing systems 2 in accordance with embodiments of the present invention are illustrated in use in an exemplary network 40. Each dispensing system 2 comprises a transmitter, such as a Bluetooth LE transmitter, within the electronics unit 10 or otherwise connected thereto. The electronics unit 10 also comprises a memory in which information (relating to each dose 38 dispensed from an inserted blister pack 30 and determined as dispensed by the sensing layer 20) is stored, the information including at least the time and date when the medicament dose 38 was dispensed. The transmitter of the dispensing system 2 transmits the data to a remote device, such as a smartphone device 42 of the patient, either continuously or at regular or irregular intervals, or when the smartphone 42 is detected as being in range of the dispensing device 2, or when power is supplied to the transmitter of the electronics unit 10, etc. In alternative arrangements, the data may be transmitted additionally or alternatively to other remote systems, such as to a computer of the patient and/or of a caregiver responsible for treatment of the patient, etc.

Figure 8A:
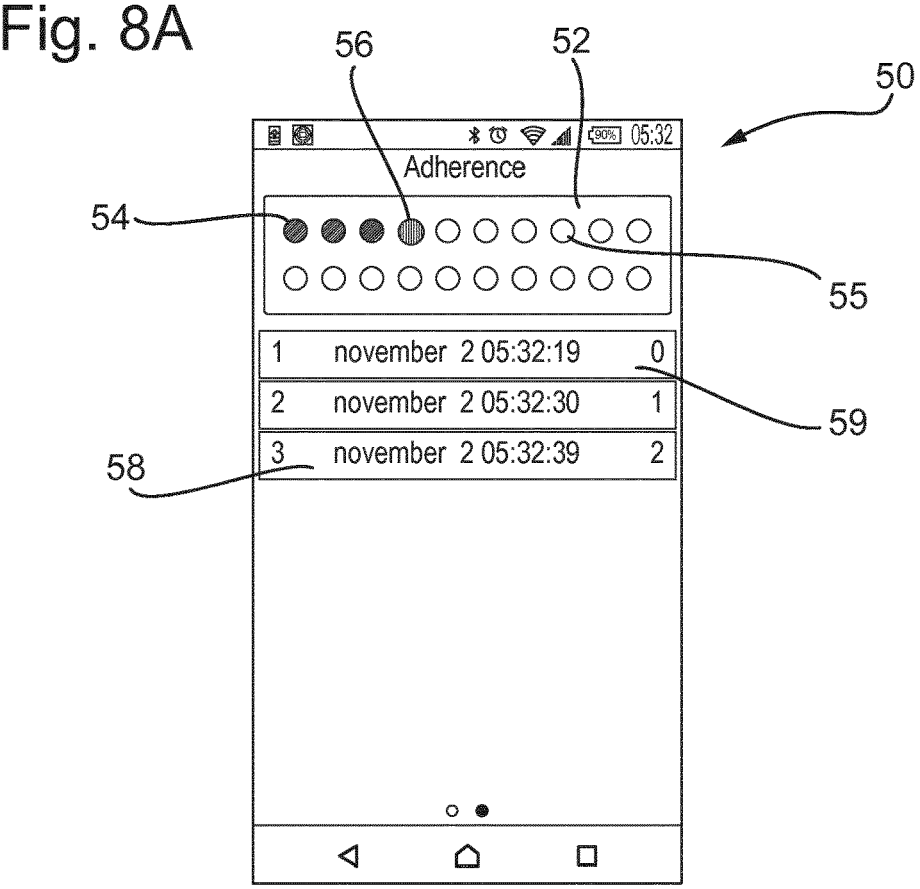
FIG. 8 illustrates examples of information transmitted from a dispensing system in accordance with embodiments of the present invention, and displayed on a device of a patient using the dispensing system.

The smartphone 42 is provided with suitable software, such as an appropriate application 50, so that the information contained in the data is displayed on the smartphone 42, as shown in FIG. 8A. Therefore the patient (or caregiver or other recipient of the data) can easily view historical data relating to each dose 38 dispensed from a blister pack using the dispensing device 2. For example, the patient can see whether they have adhered to the treatment regimen, for example as indicated with a traffic light arrangement 52 as shown in FIG. 8A (where colours may be used on the display device but are not shown in the Figures). The "green" indicators 54 illustrate that a dose 38 has been dispensed at the appropriate time with "red" indicators 56 showing that a dose 38 was not dispensed when it should have been. The "white" indicators 55 show doses 38 that have yet to be dispensed but are not yet due to be taken. The position of the dose 38 in the blister pack 30 may be indicated with a display 52 having the same number and arrangement of blisters 32 as the blister pack 30, for example. The application 50 may additionally or alternatively show other information 58 to the patient, such as the exact time and date of dispensing each dose 38 and which dose 38 in the treatment regimen was taken (i.e. the first, second, third, etc., dose), with the zeroth dose 59 indicating when a new blister pack 30 is inserted into the dispensing device 2 and thus begins a new treatment regimen.

Figure 8B:
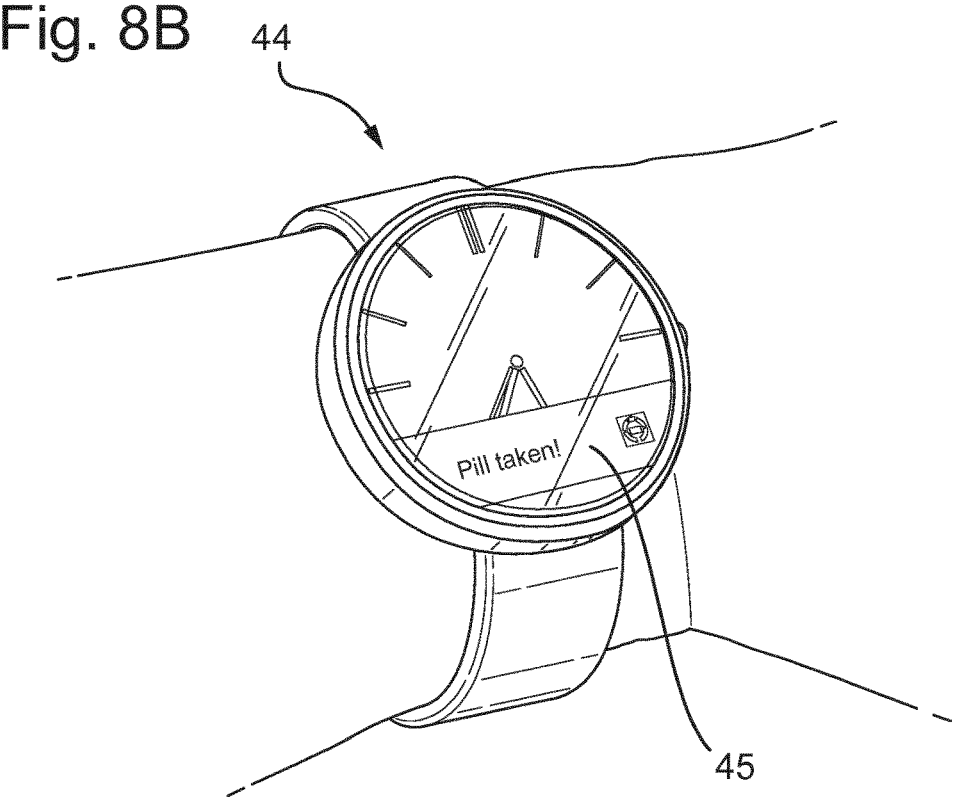

Additionally or alternatively, as shown in FIG. 7, information regarding dispensed doses 38 can be sent from the dispensing system 2 directly or indirectly (e.g. via a smartphone 42 as illustrated in the Figure) to another device of the patient, such as a smartwatch 44. For example, an indicator 45 may be triggered on the patient's smartwatch 44 immediately on dispensing a dose 38, to inform the patient that the dose 38 they have taken has been successfully registered as shown in FIG. 8B. Other information, including the same information as may be displayed on the application 50 of the smartphone 42 can also or alternatively be displayed on the smartwatch 44.

As also shown in FIG. 7, data from the dispensing system 2 may additionally or alternatively be transmitted to another remote location, such as a server 46, etc. This facilitates long term storage of the data and allows, for example, a caregiver such as a physician to access the data if the data is available from the server 46 via the Internet without the patient needing to attend the physician's office or the like.

The above embodiments comprise pressure sensing arrangements but alternative embodiments having alternative sensing layers are also contemplated within the scope of the present invention. For example, as illustrated in FIG. 10, an induction sensitive layer 122 (or inductive layer 122) is disclosed, which may be used in any suitable embodiment described above or below instead of a pressure sensitive layer 22. The inductive layer 122 comprises an induction coil layer 126 (or any other suitable means in which an electromotive force may be induced) and an induction coil substrate 124. When the induction coil layer 126 and induction coil substrate 124 are deformed (for example due to pressure P applied to the layers as per the embodiment illustrated in FIGS. 9A to 9C), a change of the electrical properties of the inductor can be detected. Therefore pressure, indicative of a dose being dispensed, is determined in the region of the coils, which surround an aperture 125 in the layer 122 through which the dose is dispensed. Alternatively, the induction coil layer 126 couples to an inductive layer in blister (34 in FIG. 3), which coupling is changed if the inductive layer in blister moves or is ruptured due to tablet removal. This change in coupling is then detected by the induction coil 126.

Figure 11A:
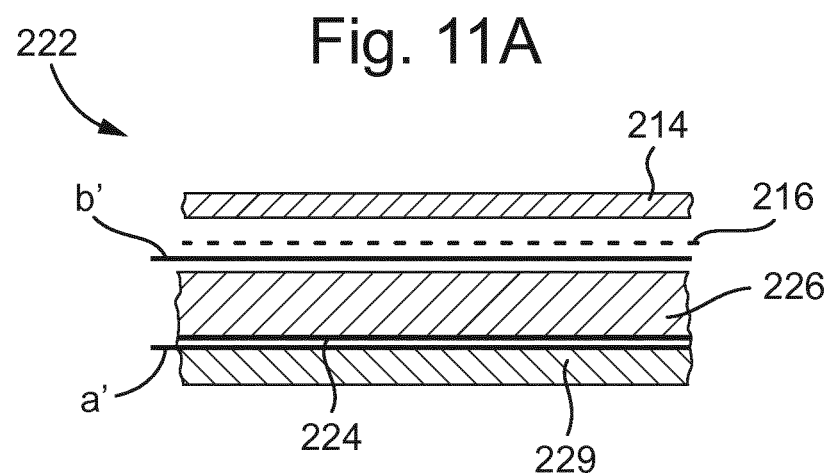
FIGS. 11A and 11B are schematic side views of a capacitive sensing layer in accordance with alternative embodiments of the present invention, in an uncompressed and compressed state respectively.
Figure 11B:
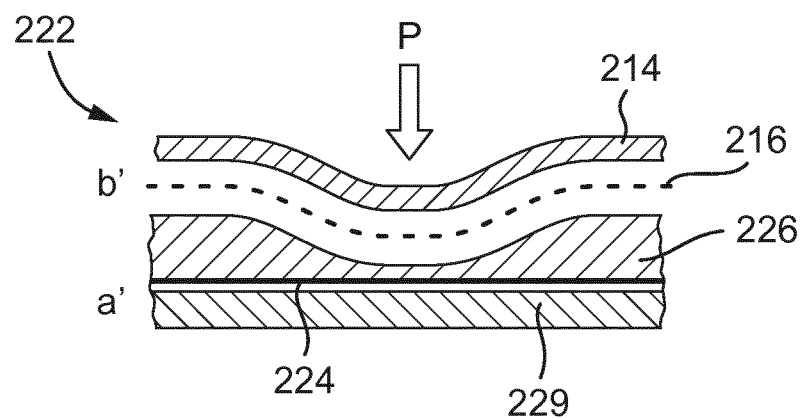

FIGS. 11A and 11B illustrate another alternative embodiment in accordance with the present invention, which comprises a capacitance sensitive layer 222 (or capacitive layer 222). Much like the inductive layer 122 embodiment described in relation to FIG. 10, this capacitive layer 222 operates on the same principle of layers being brought closer together and thus, in this case, the capacitance of the layers alters and thereby indicates pressure applied to the layers in bringing them together. In more detail, capacitive layer 222 comprises a substrate 229 with a first capacitor layer 224 above the substrate 229. A foam layer 226 is provided between the first capacitor layer 224 and a second capacitor layer 216, these two capacitor layers 224, 216 forming a capacitor having a capacitance $C_u$. Also provided are other suitable layers such as a protective layer 214 as in other embodiments. As pressure P is applied to the capacitive layer 222 (as a dose is pushed from a blister—not shown), the capacitor layers 224, 216 are brought into closer proximity, changing the capacitance $C_u$ (from the uncompressed state) to a different capacitance $C_c$ in the compressed state (e.g. increasing the capacitance). Thus the change in capacitance is indicative of a dose being dispensed from a blister pack associated with the capacitive layer 222.

Figure 12A:
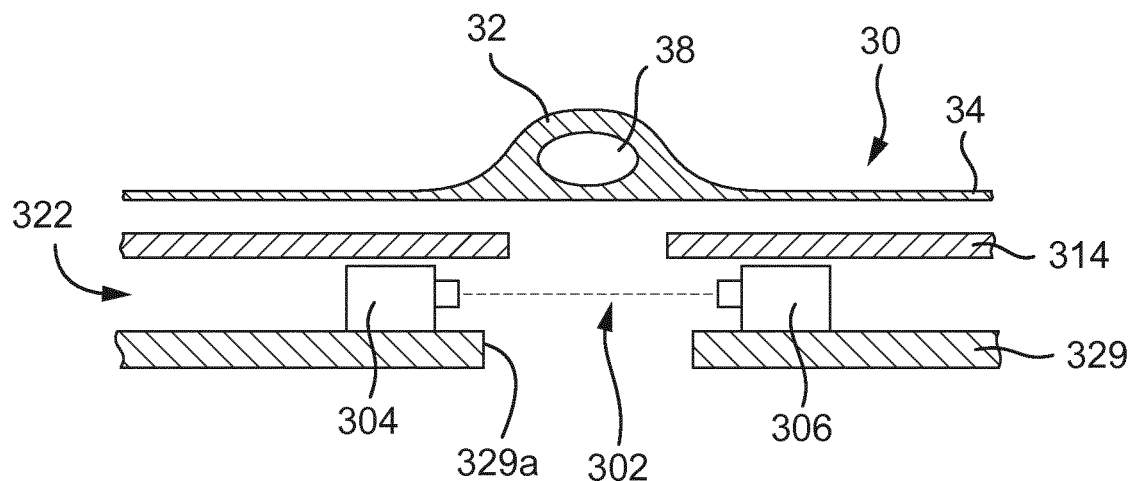
FIG. 12A is a schematic side view of an optical sensing layer in accordance with alternative embodiments of the present invention.
Figure 12B:
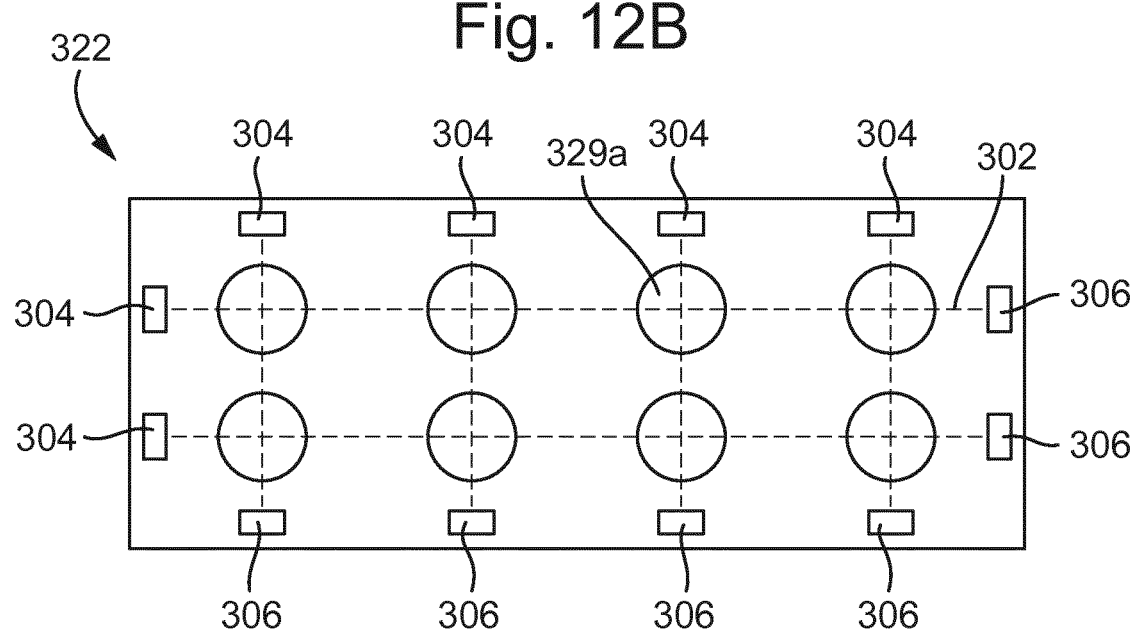
FIG. 12B is a schematic top view of the optical measuring layer of FIG. 12A.

FIGS. 12A and 12B illustrate another alternative embodiment in accordance with the present invention, which comprises an optical sensitive layer 322 (or optical layer 322). In the illustrated embodiment, a blister pack 30 is shown above the optical layer 322 having a blister 32 containing a unit dose of medicament 38. Beneath the blister pack 30 the optical layer 322 comprises a substrate 329 with at least one optical transmitter 304 aligned across an aperture 329a in the substrate 329 with at least one optical receiver 306. The optical transmitter 304 is configured to emit, either continuously or intermittently (for example only when powered and/or at regular intervals), a light beam 302 in the direction of a corresponding optical receiver and across a corresponding aperture 329a. If a dose 38 is dispensed from the blister pack 30 and passes through the aperture 329a, the light beam 302 is temporarily interrupted by the passage of the dose 38 and thus dispensing of a dose 38 is detected. FIG. 12B illustrates a top view of the optical layer 322, illustrating that a plurality of corresponding transmitters 304 and receivers 304 may be used to detect dispensing through each aperture 329a in the substrate 329. Of course, other configurations of this layer are within the scope of the invention. Furthermore, other layers from earlier embodiments, for example a protective layer 314, may also be provided in this optical embodiment.

Figure 13A:
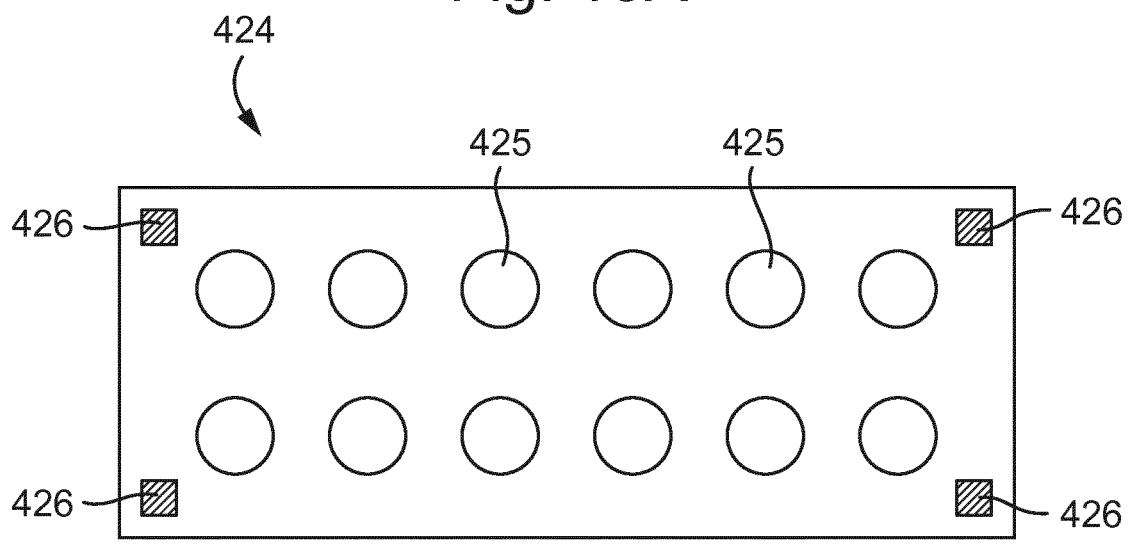
FIGS. 13A and 13B are schematic top views of conductive layers with conductive regions in accordance with alternative embodiments of the present invention.
Figure 13B:
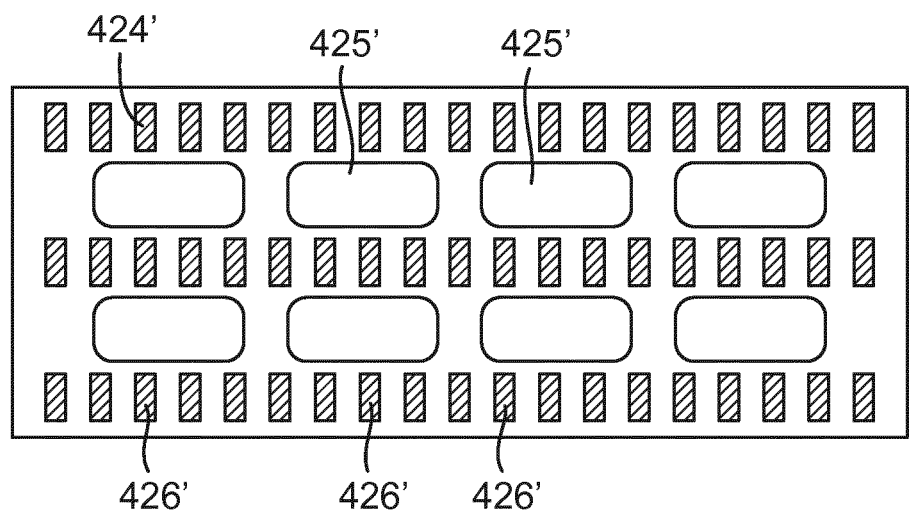

The above embodiments are illustrative of arrangements in accordance with the present invention, but are non-limiting and the scope of the invention is defined by the claims. It will be appreciated that other arrangements of each of the above examples are possible. For example, other resistive embodiments are illustrated in FIGS. 13A to 13B and 14A to 14B. FIGS. 13A and 13B illustrate two, alternative arrangements of the conductive regions of a conductive layer. In FIG. 13A, the conductive regions 426 do not surround each of the apertures 425 in the conductive layer 424, but instead are located at the corners of the conductive layer 424. This simplified structure will still detect pressure applied to a pressure sensitive (or other) layer associated therewith (not shown) and is simpler to manufacture. Another arrangement is illustrated in FIG. 13B, which has multiple conductive regions 426' arranged in an array around prolonged apertures 425', through which doses from multiple cavities of the blister pack can be dispensed. This provides a more accurate, compared to the arrangement of FIG. 13A, determination of from where a dose is dispensed, but at the same time providing a more generic configuration able to accommodate broader blister cavity arrangements, thus allowing for possible reduction of manufacturing costs due to reduced number of adaptations needed for each particular product blister.

Figure 14A:
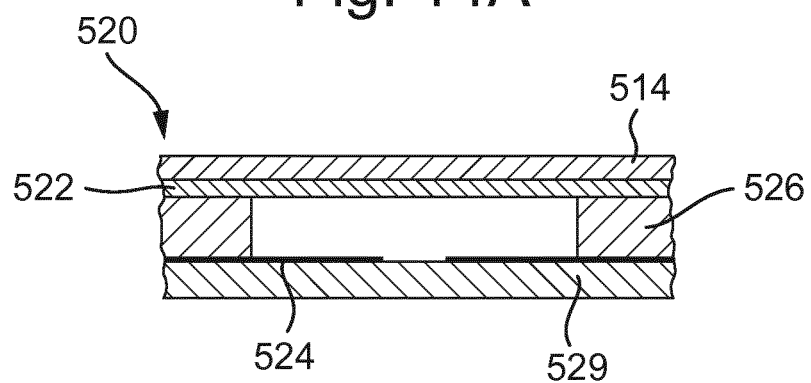
FIGS. 14A and 14B are schematic side views of a sensing layer in accordance with alternative, simplified embodiments of the present invention.
Figure 14B:
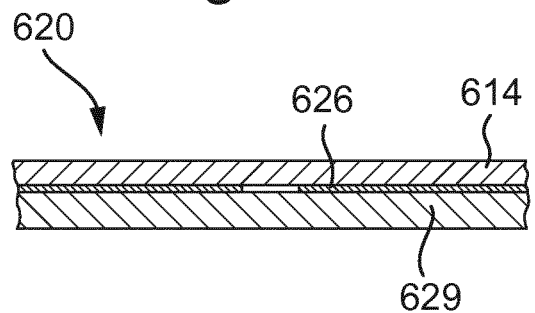

It will also be appreciated that although in some embodiments above multiple layers form the sensing layer and/or are associated therewith, not all embodiments require all these layers and/or additional layers may be provided as required. FIG. 14A illustrates a simplified sensing layer 520, which is similar to the sensing layer 20 of FIG. 9A, and comprises a protective layer 514, a foam layer 526, a conductive layer 524 and a substrate 529, but comprises a combined pressure sensitive and contact layer 522. FIG. 14B illustrates a further simplified sensing layer 620, which is similar to the sensing layer 20 of FIG. 14A, and comprises a protective layer 614 and a substrate 629, but comprises a combined pressure sensitive, foam, conductive and contact layer 626. It will be understood therefore that many modifications can be made to embodiments of the present invention without departing from the scope of the invention, as defined by the appended claims.

A method of using the dispensing system 2 of some of the various embodiments is now described. A patient is provided with the dispensing device 2, either with a full blister pack already inserted into the housing 4, or separately from the blister pack 30, which may be dispensed to the patient in a separate transaction from the pharmacy for example. In this latter case, the patient simply inserts the blister pack 30 into the housing 4, for example dropping or sliding the blister pack 30 into place between the edges 4a, 4b of the housing 4 and the ends defined by the cover 6 and the opposite end 4c. The blister pack 30 is a close fit inside the housing 4, thus ensuring good alignment of the blisters 32 with the apertures 23, 25, 27 in the sensing layer 20.

In this rest configuration, voltage from the power source is provided to the conductive layer 24, but the pressure sensitive layer 22 is isolated from the conductive layer 24 by the air gap 21 defined by the larger apertures of the foam layer 26. Therefore the dispensing system 2 is in a lower power mode, saving the e.g. battery power until it is desired to dispense a dose 38.

The patient may receive a reminder from the dispensing system 2 to prompt the patient to take a dose 38 at the appropriate time, or may otherwise determine a dose 38 should be dispensed. To do so, the patient simply pushes downwardly on a particular blister 32, as generally indicated by arrow P in FIG. 3. Pressure on the cavity 32 from the patient's finger or thumb or the like, pushes the dose 38 into contact with the seal 36 of the blister base 34 and through the seal 36 which is configured to rupture under such pressure. The dose 38 thus drops out of the dispensing system 2 through the holes 23, 25, 27 in the sensing layer 20 and the housing apertures 5 and the patient can take the dose 38.

As the patient pushes downwardly on the blister 32, not only is a dose 38 pushed through the seal 36 and out of the dispensing system 2, but also the foam layer 26 of the sensing layer 20 is compressed. This brings the pressure sensitive layer 22 and the conductive layer 24, 24' closer together and if the foam layer 26 is configured to be sufficiently compressible, the pressure sensitive layer 22 and the conductive layer 24, 24' can be pressed into direct electrical contact, by virtue of the portions of each layer 22, 24, 24' being exposed to each other due to the larger apertures 27 of the foam layer 26. Voltage is therefore provided to the pressure sensitive layer 22 by this direct electrical contact with the conductive layer 24, 24'. Thus, only when it is necessary to dispense a dose 38 is voltage provided in a timely manner to the pressure sensitive layer 22 and this layer is used to sense the pressure applied to the blister 32, for example by measuring the change in resistance of the pressure sensitive layer 22 as it is compressed. The electronics unit 10 stores this information regarding the change in resistance of the pressure sensitive layer 22 and either transmits the information for further processing to a remote device 42, 44, 46 and/or processes the information to determine the time/date of the dose 38 being dispensed. In other illustrated embodiments, the sensing layer senses a different change or variation in state to determine that a dose has been dispensed, for example a change in capacitance (as shown in FIG. 11), or an interruption of a light beam (as shown in FIG. 12), or an induced voltage (as shown in FIG. 10), etc.

In some embodiments, the sensing layer 20 is a removable component from the housing 4. If a different blister pack 30 is to be used with the dispensing system 2, a different sensing layer 20 having a configuration that corresponds with the configuration of the different blister pack 30 can be inserted into the housing 4 in replacement for the existing sensing layer 20. If the housing 4 comprises apertures 5 in an array generally corresponding to the blisters 32 of the blister pack 30, then the base 7 of the housing 4 may be configured to be removable from the remainder of the housing 4 and a replacement base 7 can be provided with a configuration corresponding to that of the different blister pack 30.

As disclosed in the various embodiments above, a modular dispensing system 2 is provided, in which standard blister packs 30 are received and in the event that a dose 38 is dispensed from a blister 32 of the blister pack 30, this is detected by the dispensing system 2 and the dispensing of a dose 38 is displayed or recorded for future reference. Thus an improved dispensing system 2 is provided, that is cost attractive, reliable, reusable, patient and manufacturing friendly, and that aids a patient in adhering to a dosing regimen and provides relevant information for review by the patient and/or a care giver as a dose 38 is dispensed and/or at an appropriate time after several doses 38 have been dispensed.

The invention claimed is:

1. A dispensing system for dispensing unit dosage forms from a blister pack, the dispensing system comprising:
   a housing for receiving a blister pack, the blister pack having a plurality of cavities with at least one unit dosage form sealed in each of the cavities, the housing comprising at least one housing aperture;
   a sensing layer comprising:
     a pressure sensitive layer configured to change resistance in response to an applied pressure;
     a conductive layer, the conductive layer comprising at least one conductive region;
     a plurality of sensing layer apertures through the pressure sensitive layer and the conductive layer, each sensing layer aperture configured to substantially align with a corresponding one or more of the plurality of cavities of the blister pack when a blister pack is received in the housing; and
     a plurality of sensing regions surrounding each sensing layer aperture that includes the pressure sensitive layer and the conductive region of the conductive layer;
   an electronics unit; and
   a power source for providing voltage to the sensing layer; wherein:
   in use, the unit dosage forms are dispensed from the blister pack through the sensing layer apertures, through the sensing regions and through the at least one housing aperture; and
   the sensing layer senses each unit dosage form being dispensed from the blister pack as a change in resistance of the pressure sensitive layer.

2. The dispensing system of claim 1, wherein the pressure sensitive layer comprises a semi-conductive material, or a non-conductive material comprising conductive particles dispersed therein.

3. The dispensing system of claim 2, wherein the pressure sensitive layer comprises a polyolefin film layer impregnated with carbon black particles.

4. The dispensing system of claim 1, wherein the sensing layer further comprises a spacing layer between the pressure sensitive layer and the conductive layer, the spacing layer spacing the pressure sensitive layer and conductive layer apart such that they are not in electrical contact, and the spacing layer being compressible such that the pressure sensitive layer and the conductive region(s) of the conductive layer can be brought into electrical contact.

5. The dispensing system of claim 1, wherein the power source provides voltage to the conductive region(s) of the conductive layer.

6. The dispensing system of claim 1, further comprising a protective layer located above the sensing layer and below the blister pack.

7. The dispensing system of claim 1, wherein the conductive layer comprises a printed circuit board (PCB), the conductive region(s) of the conductive layer being printed onto the conductive layer.

8. The dispensing system of claim 1, wherein the sensing layer is configured to measure the change in resistance and determine the profile of the pressure applied to the sensing layer to determine if:
   a unit dosage form has been dispensed from the blister pack; or
   the pressure has a non-dispensing pressure profile.

9. The dispensing system of claim 1, wherein the housing comprises a plurality of housing apertures, the housing apertures arranged in an array such that each housing aperture substantially aligns with at least one of the plurality of cavities of the blister pack when a blister pack is received in the housing, the blister pack being a standard blister pack.

10. The dispensing system of claim 1, wherein the electronics unit comprises a memory for storing data corresponding to at least the time and date at which the sensing layer senses each unit dosage form being dispensed from the blister pack.

11. The dispensing system of claim 1, wherein the housing and the sensing layer are separable components and are configured such that sensing layers with different configurations are each receivable in the housing.

12. The dispensing system of claim 1, wherein the electronics unit is configured for any one or more of the following: detecting an identification of a blister pack from a memory of the blister pack having the identification stored therein; detecting the presence of a blister pack within the housing; detecting removal of a blister pack from the housing; detecting insertion or a blister pack into the housing; and/or detecting the orientation of the blister pack within the housing.

13. A dispensing system for dispensing unit dosage forms from a blister pack, the dispensing system comprising:
   a housing for receiving a blister pack, the blister pack having a plurality of cavities with at least one unit dosage form sealed in each of the cavities, the housing comprising at least one housing aperture;
   a sensing layer comprising:
     an induction coil layer comprising one or more induction coils;
     a flexible induction coil substrate;
     a plurality of sensing layer apertures through the induction coil layer and the flexible induction coil substrate, each sensing layer aperture configured to substantially align with a corresponding one or more of the plurality of cavities of the blister pack when a blister pack is received in the housing; and
     a plurality of sensing regions defined by the one or more induction coils and surrounding each sensing layer aperture;
   an electronics unit; and
   a power source for providing voltage to the sensing layer; wherein:
   in use, the unit dosage forms are dispensed from the blister pack through the sensing layer apertures, through the sensing regions and through the at least one housing aperture; and
   the sensing layer senses each unit dosage form being dispensed from the blister pack as a deformation of the induction coil layer and the flexible induction coil substrate causing a change in electrical properties of the sensing regions.

14. The dispensing system of claim 13, wherein the housing comprises a plurality of housing apertures, the housing apertures arranged in an array such that each housing aperture substantially aligns with at least one of the plurality of cavities of the blister pack when a blister pack is received in the housing, the blister pack being a standard blister pack.

15. The dispensing system of claim 13, wherein the electronics unit comprises a memory for storing data corresponding to at least the time and date at which the sensing layer senses each unit dosage form being dispensed from the blister pack.

16. The dispensing system of claim 13, wherein the housing and the sensing layer are separable components and are configured such that sensing layers with different configurations are each receivable in the housing.

17. The dispensing system of claim 13, wherein the electronics unit is configured for any one or more of the following: detecting an identification of a blister pack from a memory of the blister pack having the identification stored therein; detecting the presence of a blister pack within the housing; detecting removal of a blister pack from the housing; detecting insertion or a blister pack into the housing; and/or detecting the orientation of the blister pack within the housing.

18. The dispensing system of claim 13, further comprising a protective layer located above the sensing layer and below the blister pack.

19. A method of dispensing unit dosage forms from a dispensing system having a blister pack received therein, the dispensing system comprising:
a housing for receiving a blister pack, the blister pack having a plurality of cavities with at least one unit dosage form sealed in each of the cavities, the housing comprising at least one housing aperture;
a sensing layer comprising:
a pressure sensitive layer configured to change resistance in response to an applied pressure;
a conductive layer, the conductive layer comprising at least one conductive region;
a plurality of sensing layer apertures through the pressure sensitive layer and the conductive layer, each sensing layer aperture configured to substantially align with a corresponding one or more of the plurality of cavities of the blister pack when a blister pack is received in the housing; and
a plurality of sensing regions surrounding each sensing layer aperture that includes the pressure sensitive layer and the conductive regions of the conductive layer;
an electronics unit; and
a power source for providing voltage to the sensing layer;
the method comprising:
sensing with the sensing layer a change in resistance of the pressure sensitive layer when each unit dosage form is dispensed from the blister pack through the sensing layer apertures, through the sensing regions and through the at least one housing aperture.

20. The method of claim 19, wherein the pressure sensitive layer comprises a semi-conductive material, or a non-conductive material comprising conductive particles dispersed therein.

21. The method of claim 19, further comprising sensing a profile of a pressure applied in a vicinity of each cavity, to determine if:
a unit dosage form has been dispensed from the blister pack; or
the pressure has a non-dispensing pressure profile.

22. A method of dispensing unit dosage forms from a dispensing system having a blister pack received therein, the dispensing system comprising:
a housing for receiving a blister pack, the blister pack having a plurality of cavities with at least one unit dosage form sealed in each of the cavities, the housing comprising at least one housing aperture;
a sensing layer comprising:
an induction coil layer comprising one or more induction coils;
a flexible induction coil substrate;
a plurality of sensing layer apertures through the induction coil layer and the flexible induction coil substrate, each sensing layer aperture configured to substantially align with a corresponding one or more of the plurality of cavities of the blister pack when a blister pack is received in the housing; and
a plurality of sensing regions defined by the one or more induction coils and surrounding each sensing layer aperture;
an electronics unit; and
a power source for providing voltage to the sensing layer;
the method comprising:
sensing with the sensing layer a change in electrical properties of the sensing regions when each unit dosage form is dispensed from the blister pack through the sensing layer apertures, through the sensing regions and through the at least one housing aperture.

23. The method of claim 22, further comprising sensing a profile of a pressure applied in a vicinity of each cavity, to determine if:
a unit dosage form has been dispensed from the blister pack; or
the pressure has a non-dispensing pressure profile.

* * * * *